United States Patent [19]

Demirel et al.

[11] 4,453,398
[45] Jun. 12, 1984

[54] ICE POROSIMETER

[75] Inventors: Turgut Demirel, Ames, Iowa; Bekir V. Enüstün, Istanbul, Turkey

[73] Assignee: Iowa State University Research Foundation, Inc., Ames, Iowa

[21] Appl. No.: 450,074

[22] Filed: Dec. 15, 1982

[51] Int. Cl.³ .......................................... G01N 15/08
[52] U.S. Cl. .......................................... 73/38; 374/45
[58] Field of Search ................. 73/38, 73, 74, 432 PS; 374/45, 54, 55, 56

[56] References Cited

U.S. PATENT DOCUMENTS

| | | | |
|---|---|---|---|
| 3,106,086 | 10/1963 | Hughel | 374/56 |
| 3,327,524 | 6/1967 | Osgood | 374/54 |
| 4,170,129 | 10/1979 | Lowell | 73/38 |

FOREIGN PATENT DOCUMENTS 647588  2/1979  U.S.S.R. .............................. 374/45

*Primary Examiner*—Gerald Goldberg
*Assistant Examiner*—Hezron Williams
*Attorney, Agent, or Firm*—Zarley, McKee, Thomte, Voorhees & Sease

[57] ABSTRACT

An ice porosimeter for the accurate and efficient derivation of measurements concerning the porosity of a porous material, which includes a mercury dilatometer having a mercury-filled reservoir with a capillary stem extending upwardly therefrom. The porous material to be analyzed is inserted into the reservoir after it is saturated with water. The temperature of the contents of the reservoir is then varied to cause the water in the porous material to change state, either freezing the water or melting the ice. A thermistor measures the temperature in the reservoir and transmits these readings to a means for recording those measurements. Concurrently, a condenser is placed surrounding the capillary stem of the dilatometer and is connected to electrical circuitry which induces a capacitance across the condenser. As the volume of the contents of the dilatometer increases or decreases with change in temperature, mercury from the reservoir moves up or down the capillary stem thereby changing the capacitance of the condenser. The volume of the pores, pore size distribution, total specific pore surface, and size of pore constrictions can then be derived by means which compares electrical capacitance across the condenser as a function of temperature as measured by the thermistor.

13 Claims, 7 Drawing Figures

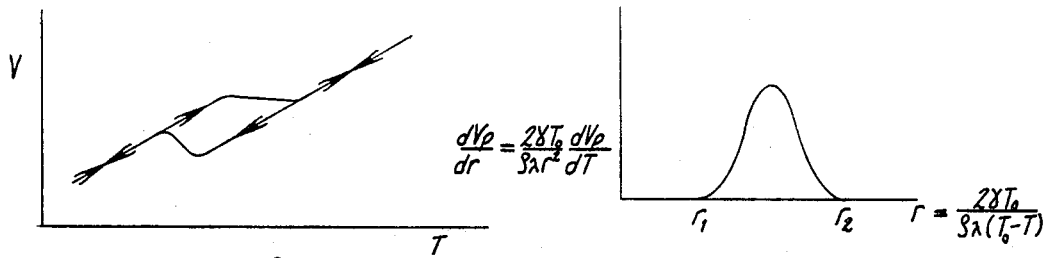
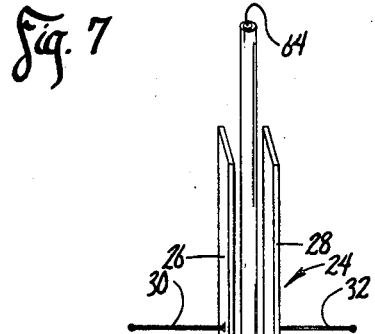
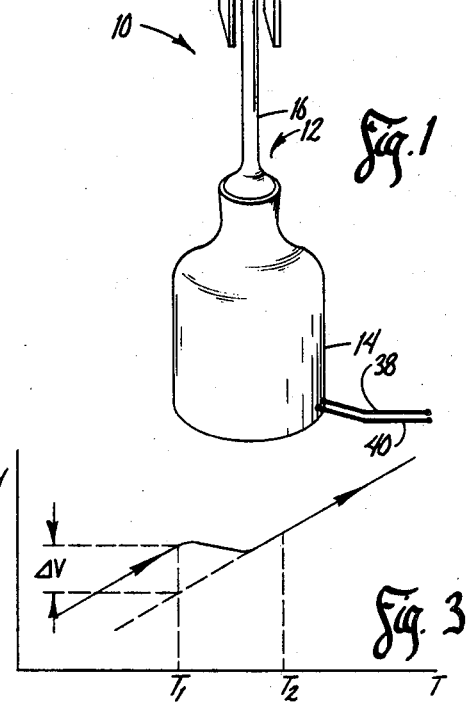
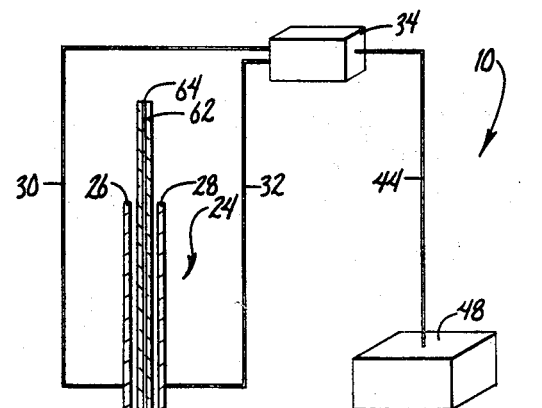
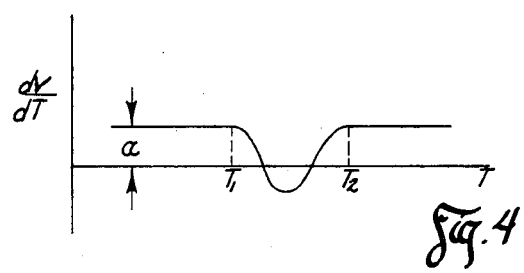

ICE POROSIMETER

BACKGROUND OF THE INVENTION

This invention relates to porosimeters, more particularly to porosimeters wherein the porous material to be analyzed is first saturated with water so that it may be frozen and thawed in the porosimeter to analyze the porosity of the material.

The pore characteristics of many materials are determinative of the advantageous utility of these materials for specific uses and tasks. For example, the adsorbancy of fine powders in chemicals catalysis is determined by the pore size and size distribution characteristics of the powder, as is the frost resistance of bricks. Therefore, there is a real need for apparatus and methods to determine and measure the pore characteristics of a variety of materials.

One method by which total pore volume and pore-size distribution is estimated is by gas-adsorption isotherms. In this method, pore volume is related to the amount of gas adsorbed on the external surface of the porous material sample in comparison with the amount adsorbed in the pores at a saturation pressure. Problems exist with this method, particularly in interpretation of the resulting measurements.

Another method of estimating porosity is the use of mercury porosimetry which derives pore volume distribution by measuring the cumulative volumes of mercury entering the porous sample material as a function of increasing pressure. This technique is based upon the principle that a minimum pressure is required to force mercury through the pore openings.

Problems can arise using this technique in that damage to the pores may occur with increasing pressure. Additionally, assumptions have to be made regarding contact angle and pore shape.

A related method of using a mercury porosimeter to measure the porosity of a porous material involves measuring the change in electrical resistance of a wire dipped in the mercury to derive the change in the volume of the mercury as pressure is increased and decreased.

As is evident, mercury porosimetry requires complex equipment and integrity of the system so that the pressure in the system can be varied accurately to derive maximum information.

Other methods exist utilizing various processes for estimating pore size and size distribution, but they basically follow the same general techniques of the methods described above and are therefore subject to the same problems.

The method of forcing mercury into the pores of the materials by increasing pressure works well for materials having nearly cylindrical pores and predictable contact angles for mercury, however, few materials exist in such a perfect state. Additionally, conventional mercury porosimetry data curves are difficult to interpret, usually having a hard to interpret hysteresis between curves plotted for pressurization and depressurization.

In order to avoid complications due to this hysteresis, attempts have been made to intrude the sample twice to more accurately determine the distribution of uniform pores, but this method is subject to contamination of the pores by the mercury and chemisorption of the mercury by the sample.

Therefore, it is an object of this invention to provide an ice porosimeter which accurately and efficiently measures pore characteristics of a porous material.

A further object of this invention is to provide an ice porosimeter from which can be derived accurate estimations of pore volume, pore size, pore-size distribution, and specific surface of porous materials, making use of changes in any property of a system which contains such a material, as a result of phase transitions taking place in it as temperature in this system changes.

A further object of this invention is to provide an ice porosimeter which can also accurately estimate the radius of pore constrictions during the freezing process.

Another object of this invention is to provide an ice porosimeter which utilizes the phase transitions of water to more accurately measure the pore characteristics of a porous material.

Another object of this invention is to provide an ice porosimeter which is simple in construction, simple to use, and simple to interpret.

A further object of this invention is to provide an ice porosimeter which is economical and efficient.

Additional objects, features, and advantages of the invention will become apparent with reference to the accompanying specification and drawings.

SUMMARY OF THE INVENTION

This invention utilizes a mercury dilatometer having a mercury-holding reservoir and a capillary stem extending upwardly from the reservoir. A temperature measuring means is positioned in the reservoir to provide temperature readings of the contents of the reservoir, while at the same time a means for detecting changes in volume of the mercury provides such measurements as a function of the temperature readings provided by the temperature measuring means.

A porous material to be analyzed is first saturated with water and then placed inside the reservoir of the dilatometer. By varying the temperature of the dilatometer, to the point that there are phase changes in the water held within the pores of the porous material, the measurements derived can be used to derive pore characteristics of the material.

BRIEF DESCRIPTION OF THE DRAWINGS

FIG. 1 is a perspective view of the invention.

FIG. 2 is a front sectional view of the invention showing schematically the electronic circuits associated with the invention.

FIGS. 3-7 are graphs illustrating the derivation of porosity information.

DETAILED DESCRIPTION OF THE PREFERRED EMBODIMENT

In reference to the drawings, and particularly FIG. 1. there is shown an ice porosimeter 10 in accordance with the invention. A mercury dilatometer 12, having a container 14 and a capillary stem 16 has a means for detecting changes in volume of mercury 20 in dilatometer 12 and a means for detecting temperature changes in mercury 20 of dilatometer 12.

By referring to FIG. 2, it can be seen that means for detecting changes in volume comprises condenser 24 having metal plates 26 and 28 positioned on opposite sides of capillary stem 16. Wire leads 30 and 32 connect condenser 24 to a capacitance bridge 34 which measures the capacitance of condenser 24 as a function of the volume of mercury in stem 16.

Means for detecting temperature changes comprises a thermistor 36 in reservoir 50. Thermistor 36 is connected by leads 38 and 40 to potentiometer 42 which records instantaneous values of temperature derived by thermistor 36. Electrical leads 44 and 46 supply the information from capacitance bridge 34 and potentiometer 42 respectively to microcomputer interface 48 connected to a microcomputer (not shown) which then computes the volume of the mercury in the dilatometer as a function of temperature and records and/or prints this output for use in deriving the pore characteristics of the material being tested.

The exact structure of the dilatometer 12 can also be seen in FIG. 2. Container 14 includes mercury holding reservoir 50 and neck 52 which defines top opening 54. Capillary stem 16 is open at both ends, having a bulb-shaped lower end 56 with lower opening 58 which fits within opening 54 of container 14 creating a seal with neck 52. Narrow stem 16 extends upwardly from bulb-shaped lower end 56 between plates 26 and 28 of condenser 24. Narrow interior channel 62 extends the length of stem 16 to upper opening 64.

In operation, the invention works as follows. Mercury holding reservoir 50 of container 14 is partially filled with mercury 20. A porous sample material 66 is first saturated with water and then inserted into the mercury holding reservoir 50. Capillary stem 16 is then positioned in opening 54 of container 14 while additional mercury 20 is introduced into mercury holding reservoir 50 so that all air is evacuated from reservoir 50 and so that the mercury 20 enters bulb-shaped lower end 56 of capillary stem 16 and fills narrow interior channel 62 for a portion of the way up of narrow stem 16. The temperature of dilatometer 12 is then gradually lowered until the water in porous sample material 66 is frozen. Condenser 24 is then operatively connected to capacitance bridge 34 which measures the capacitance across metal plates 26 and 28. Thermistor 36 is operatively connected to potentiometer 42 which monitors changes in temperature of the mercury 20 in mercury holding reservoir 50. Capacitance bridge 34 and potentiometer 42 are in turn operatively connected to microcomputer interface 48 which takes the measurements of change in capacitance of condenser 24 derived by capacitance bridge 34 and takes the measurements of change of temperature derived by thermistor 36 and potentiometer 42 and feeds the measurements into the microcomputer. The microcomputer computes the total volume of the contents of the dilatometer 12 at any given moment as the ice contained in porous sample material 66 melts over time.

When a porous material saturated with water is frozen, the volume of this system increases as a result of expulsion of some ice out of the pores due to the expansion of water upon freezing. This expansion is 9% of the volume of water present in the sample. On rewarming, the process is reversed, and from the measured contraction as a function of temperature, pore volume, pore size distribution and specific surface of the porous sample material 66 can be determined.

The melting point of ice T in the pores of the sample material is related to the radius r of the pores by equation (1).

$$r = 2\gamma T_o / \pi\lambda (T_o - T) \quad (1)$$

where $T_o = 273.2°$ K. (normal melting point of ice, $\gamma = 29$ erg/cm$^2$ (ice/water interfacial tension at 273.2° K.), $\lambda = 80$ Cal/g (latent heat of fusion of ice), and $\rho = 1$ g/cm$^3$ (density of water). Therefore melting starts at a temperature $T_1$ (FIGS. 3 and 4) in the smallest pores of the sample material and it completes melting at $T_2$ (FIGS. 3 and 4) in the largest pores. By measuring the volume of the sample material between these limits as a function of temperature, pore size distribution of the sample material can be obtained through equation (1) as follows:

The sample material is saturated and placed in mercury dilatometer 12, frozen and allowed to rewarm gradually. Let $V_s$ be the volume of the sample material, $V_m$ the volume of the mercury and V the total volume of the contents of the dilatometer 12. Then, $$dV/dT = dV_s/dT + dV_m/dT \quad (2).$$

Since for thermal expansion of mercury we have $$dV_m/dT = a \quad (3)$$

where a is a temperature independent constant, from equations (2) and (3) the following is derived:

$$dV/dT = dV_s/dT + a \quad (4)$$

It follows that outside the temperature interval $T_1$, $T_2$ the total volume V changes linearly with temperature. Any deviation from linear indicates a phase change (in this case, melting). A typical graphic plot of volume as a function of temperature is shown in FIG. 3.

Therefore, by utilizing the ice porosimeter 10 to derive measurements of volume as a function of temperature, determinations and estimations of pore characteristics of a sample material can be computed using the above described equations.

The total volume change $\Delta V$ can be found by a linear extrapolation as shown in FIG. 3. The pore volume $V_p$ is given by $$V_p = \Delta V / 0.09 \quad (5).$$

The derivative of the curve in FIG. 3 will appear as shown in FIG. 4. Since a small fraction of pore volume $dV_p$ in which ice is transformed into liquid water is given by $dV_p = dV_s/0.09$, then $$dV_p/dT = -dV_s/dT = /0.09 \quad (6).$$

From equations (4) and (6)

$$dV_p/dT = -dV/dT - a = /0.09 \quad (7).$$

Through transformation $dV/dT \rightarrow dV_p/dT \rightarrow dV_p/dr$ by equations (1) and (7) and $T \rightarrow r$ by equation (1), the actual (volume) pore size distribution is obtained as shown in FIG. 5.

If $dV_p$ is the volume of a differential pore volume element of height dh, and dA is the corresponding pore surface, then $$dV_p = \pi r^2 dh \quad (8)$$

and $$dA = 2\pi r \, dh \quad (9).$$

From equations (8) and (9) we obtain $$dA/dr = (2/r) \, dV_p/dr \quad (10).$$

Therefore, after transformation $dV_p/dr \rightarrow dA/dr$ by equation (10) and by drawing dA/dr vs. r curve, total pore surface A can be determined by integration as shown in FIG. 6. The specific surface is calculated by dividing A by the mass of the sample material.

The accuracy in determination of pore volume, pore size distribution, and specific surface of the sample material can be improved by taking into account variation of γ with temperature using the relationship disclosed by B. V. Enüstün, H.S. Senturk & O. Yurdakul, as disclosed in 65 J. Col. Int. Sci. 509 (1978);

$$\gamma = 29 + 0.25(T - 273.2) \text{ erg/cm}^2 \quad (11)$$

and substituting in equation (1).

If similar measurements are taken also during freezing process and necessary computations are made, the radius of pore constrictions can be estimated. (see Enüstün et al, supra.). The general form of the graphic plot of total volume V versus temperature T, revealing cooling/rewarming hysteresis is shown in FIG. 7.

It should be noted that plates 26 and 28 of condenser 24 could alternatively be replaced by an elongated tubular metal member positioned around capillary stem 16.

The above description pertains to the preferred embodiment of the invention only. Modifications can be made while staying within the boundries of the invention.

What is claimed is:

1. An ice porosimeter for deriving measurement concerning porosity of a water-saturated porous material by varying the temperature of the contents of said porosimeter comprising:
   (a) a mercury dilatometer having a mercury-holding reservoir and a capillary stem in fluid communication with and extending upwardly from said reservoir, said reservoir being adapted to hold said porous material;
   (b) a means for measuring instantaneous temperature values for the contents of said reservoir;
   (c) condenser means operatively positioned around said capillary stem and connected to an electronic circuit for creating an electrical capacitance and continuously measuring the capacitance across said capillary stem; and
   (d) means for deriving the volume of the pores, pore size distribution, total specific pore surface, and size of pore constrictions of said porous material from the measurements from said condenser means as a function of the corresponding measurements from said means for measuring instantaneous temperature values.

2. The device of claim 1 wherein said means for measuring instantaneous temperature values comprises a thermistor operatively connected to a potentiometer.

3. The device of claim 1 wherein said condenser means comprises a capacitor having two metal plates disposed on opposite sides of said capillary stem connected to an electronic circuit for creating an electrical capacitance and continuously measuring the capacitance across said capillary stem.

4. The device of claim 1 wherein said condenser means 1 comprises a capacitor of tubular configuration positioned surrounding said capillary stem and being connected to an electronic circuit for creating an electrical capacitance and continuously measuring the capacitance across the capillary stem.

5. The device of claim 1 wherein said electronic circuit for creating an electrical capacitance and continuously measuring the capacitance across said capillary stem comprises a capacitance bridge.

6. The device of claim 1 further comprising a means for recording and printing instantaneous corresponding values of temperature from said means for measuring instantaneous temperature values, capacitance from said condenser means, and said derived values of pore volume, pore size distribution, total specific pore surface, and size of pore constrictions.

7. The device of claim 6 wherein said means for recording and printing instantaneous corresponding values of temperature further comprises a microcomputer interface operatively connected to a microcomputer, said microcomputer interface being operatively connected to said means for measuring instantaneous temperature values and said condenser means.

8. The device of claim 1 wherein said means for deriving the volume of the pores of said sample further comprises means for deriving the pore size distribution of said sample.

9. The device of claim 1 wherein said means for deriving the volume of the pores of said sample further comprises means for deriving the total specific pore surface of said sample.

10. The device of claim 1 further comprising means for deriving the size of pore constrictions.

11. A method for computing the pore volume, pore size, pore size distribution, and specific surface of a porous material comprising the following steps:
    (a) saturating said porous material with water;
    (b) placing said saturated porous material into a mercury dilatometer;
    (c) varying the temperature of the contents of said dilatometer to cause said saturated porous material to change states;
    (d) measuring the changes in total volume of the contents of said dilatometer as a function of temperature;
    (e) calculating the volume of said porous material as a function of temperature;
    (f) calculating the volume of the mercury in said mercury dilatometer as a function of temperature;
    (g) computing pore volume, pore size distribution, specific pore surface from the measurements of steps d, e, and f.

12. The method of claim 11 wherein the measurements of steps d, e, and f, are taken after the temperature is decreased to the point where the water in said porous material is frozen, the temperature then being gradually increased until melting of the water in said porous material has occured.

13. The method of claim 11 wherein said measurements of steps d, e, and f are taken during the adjustment of the temperature in the dilatometer downward until the water in said porous material is frozen so that size of pore constrictions may be derived.

* * * * *